(12) United States Patent
Piret

(10) Patent No.: US 7,766,014 B2
(45) Date of Patent: Aug. 3, 2010

(54) ARTICLE AND METHOD FOR ABSORBING BODILY SUBSTANCE DISCHARGE FROM AND DELIVERING MEDICINAL SUBSTANCE TO MOUTH OR NOSE

(76) Inventor: Wendy P. Piret, 8862 SE. 37th St., Mercer Island, WA (US) 98040

( * ) Notice: Subject to any disclaimer, the term of this patent is extended or adjusted under 35 U.S.C. 154(b) by 348 days.

(21) Appl. No.: 11/879,350

(22) Filed: Jul. 17, 2007

(65) Prior Publication Data

US 2009/0024102 A1    Jan. 22, 2009

(51) Int. Cl.
*A61M 11/00*    (2006.01)

(52) U.S. Cl. ............... 128/204.13; 128/200.24; 606/199

(58) Field of Classification Search ............ 128/204.13, 128/200.24, 204.12; 606/199
See application file for complete search history.

(56) References Cited

U.S. PATENT DOCUMENTS

| | | | |
|---|---|---|---|
| 4,244,057 A | 1/1981 | Burnham | |
| 4,479,329 A | 10/1984 | Fraden | |
| 4,536,889 A | 8/1985 | Taylor et al. | |
| 4,671,267 A * | 6/1987 | Stout | 602/2 |
| 4,675,009 A * | 6/1987 | Hymes et al. | 604/304 |
| 6,090,403 A * | 7/2000 | Block et al. | 424/447 |
| 6,295,982 B1 * | 10/2001 | Reed, Jr. | 128/200.24 |
| 6,399,192 B1 * | 6/2002 | Pinna et al. | 428/353 |
| 6,430,764 B1 * | 8/2002 | Peters | 5/641 |
| 6,569,136 B1 | 5/2003 | Tao et al. | |
| 6,579,273 B2 | 6/2003 | Dupuy | |
| 6,688,305 B1 * | 2/2004 | Perry | 128/202.16 |
| 6,769,428 B2 * | 8/2004 | Cronk et al. | 128/200.24 |
| 2007/0118943 A1 | 5/2007 | Stockhamer | |

* cited by examiner

*Primary Examiner*—Steven O Douglas
(74) *Attorney, Agent, or Firm*—James Ray & Assoc

(57) ABSTRACT

The present invention provides a wearing article for absorbing bodily substance discharge from mouth or nose. The article is formed from a material which is capable of receiving a holding bodily substance device and which is simply retained on the forearm or elbow of the user. The invention also provides a wearing article for delivering medicinal substance to mouth or nose.

4 Claims, 3 Drawing Sheets

ARTICLE AND METHOD FOR ABSORBING BODILY SUBSTANCE DISCHARGE FROM AND DELIVERING MEDICINAL SUBSTANCE TO MOUTH OR NOSE

FIELD OF THE INVENTION

The present invention relates, in general, to absorbent articles and, more particularly, this invention relates to a wearing article for absorbing bodily substance discharge from and delivering medicinal substance to mouth or nose.

BACKGROUND OF THE INVENTION

As is generally well known, many often must continue to work, travel or attend school regardless of their coughing, sneezing and having runny noses. Many use proper etiquette and considerations to others by covering mouth and nose or using a tissue while some have no regards to the safety and well being of others. Thus, public places, such as classrooms, office buildings and airplanes are a breezing ground for airborne germs and bacteria due to these sick individuals not taking proper precautions when sneezing or coughing. Some individuals, who are cognoscente of their surroundings and are trying to prevent the spread of germs but cannot easily and timely locate tissue or handkerchief, sneeze or cough into their forearm or the crook of the elbow, either bare or covered by clothing. While such method limits the spread of harmful germs, the discharged substance during coughing or sneezing remains on the skin or on the clothing and potentially endangers those who come in contact with such skin or clothing. Also, the discharged substance is often visible on the clothing surface which is undesirable to those who must maintain proper and clean appearance and cannot timely change their clothing. Even properly disposing of used tissue may be a cumbersome task due to unavailability of trash receptacles causing the used tissue to be placed into a pocket or left on the surface where it may come in contact with others.

It is especially difficult for young children to learn and remember proper techniques of how to cover their mouth and nose causing the children to cough or sneeze into their hands or into air and leading to the rampant spread of coughs and runny noses throughout the classroom or childcare facility.

SUMMARY OF THE INVENTION

According to one embodiment, the invention provides an article which is worn on an arm of a user for absorbing bodily substance discharge from mouth or nose. The article includes means which is engageable with such user arm for receiving and holding such bodily substance discharge. A retaining means is provided for retaining the receiving and holding means on such arm in a semi-permanent manner.

According to another embodiment of the invention, therein is provided a method of absorbing bodily substance discharge from mouth or nose. The method includes the step of providing an article capable of receiving and holding the bodily substance discharge. Then, attaching the article to a portion of an arm. Next, positioning the portion of the arm having the article attached thereon in front of the mouth or the nose. Finally, expelling the bodily substance discharge into the article.

According to yet another embodiment, the present invention provides a method of delivering at least one medicinal substance to mouth or nose. The method includes the step of providing an article capable of absorbing the at least one medicinal substance. Next, incorporating the at least one medicinal substance into the article. Then, attaching the article to a portion of an arm. Positioning the portion of the arm having the article attached thereon in front of the mouth or the nose. Finally, receiving, by the user, the at least one medicinal substance incorporated into the article.

OBJECTS OF THE INVENTION

It is, therefore, one of the primary objects of the present invention to provide an article for absorbing bodily substance discharge from mouth or nose.

Another object of the present invention is to provide an article for absorbing bodily substance discharge from mouth or nose which can be conveniently worn on the forearm, elbow or upper arm of the user.

Yet another object of the present invention is to provide an article for absorbing bodily substance discharge from mouth or nose which can be easily disposed after use.

A further object of the present invention is to provide an article for absorbing bodily substance discharge from mouth or nose which can periodically emit audible messages reminding the user to use such article.

Yet a further object of the present invention is to provide an article for absorbing bodily substance discharge from mouth or nose which can be reused after washing or cleaning.

An additional object of the present invention is to provide an article for absorbing bodily substance discharge from mouth or nose which has medicinal substance disposed therein for soothing the mouth or nose coming in contact with such article.

Another object of the present invention is to provide a method of using the aforedescribed article.

A further object of the present invention is to provide an article for delivering medicinal substance to mouth or nose.

Yet a further object of the present invention is to provide an article for delivering medicinal substance to mouth or nose which enables the user to inhale such medicinal substance.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE VARIOUS EMBODIMENTS OF THE INVENTION

Figure 1:
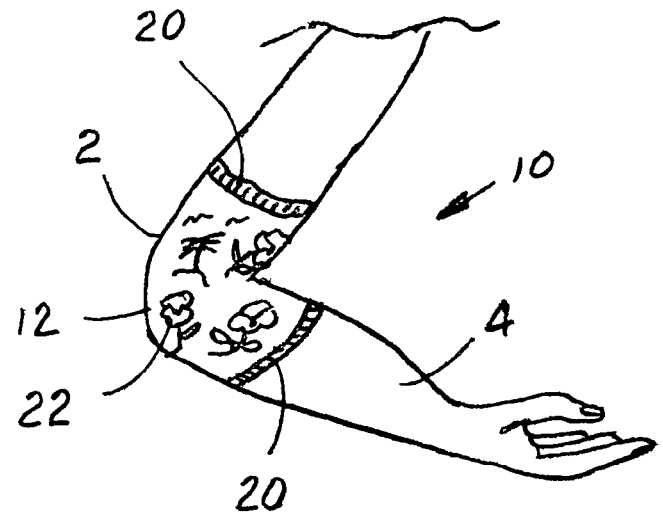
FIG. 1 is a perspective view of an article for absorbing bodily substance discharge from and delivering medicinal substance to mouth or nose which is constructed according to one embodiment of the invention and which is shown as being worn on the elbow of the user.

Prior to proceeding to the more detailed description of the present invention, it should be noted that, for the sake of clarity and understanding, identical components which have identical functions have been identified with identical reference numerals throughout the several views illustrated in the drawing figures.

Reference is now made, to FIGS. 1-8, wherein there is shown an article, generally designated as 10, for absorbing bodily substance discharge from and delivering medicinal substance to mouth or nose. As is generally known, a cough and, particularly a productive cough, brings up a mixture of mucus, irritants, and other substances from the lungs. A dry cough does not bring up this mixture but does bring up and expel harmful bacteria.

It is further generally known that sneezing is the response of the mucous membrane of the nose to an irritant or foreign body that causes allergy in a hypersensitive person. Sneezing manifests itself as an involuntary explosive burst of air from the nose and mouth that removes and expels offending material from the nasal passages.

Thus, it is to be understood that the definition of a bodily substance discharge applies to mucus, irritants, bacteria, other substances and various combinations thereof discharged through the mouth or nose.

In accordance with one aspect of the invention, the article 10 includes means for receiving and holding such bodily substance discharge and a retaining means for retaining the receiving and holding means on a portion of an arm in a semi-permanent manner.

Figure 2:
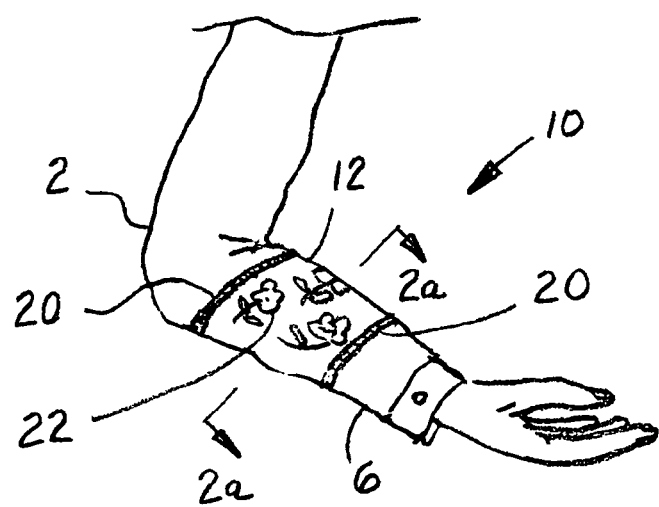
FIG. 2 is a perspective view of the article of FIG. 1, shown as being worn on the forearm of the user.
Figure 2A:
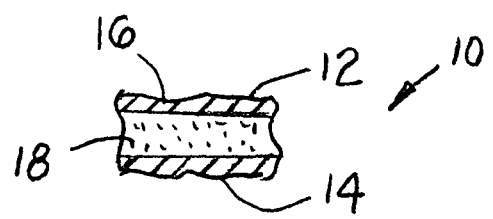
FIG. 2a is a cross-sectional view of the article of FIG. 1 along lines 2a-2a of FIG. 2.

According to one embodiment of the invention, the means for receiving and holding such bodily substance discharge includes cloth member 12 which is manufactured from pure cotton or hemp/cotton combination material which is extensively used in cloth diapers, as for example, being manufactured by Green Mountain Diapers Corporation of Vernon, Vt. This material is washable and therefore can be reused repeatedly. Since the material does not contain micro fibers or polyester materials typically associated with conventional diapers, it is advantageous for use by those who are conscious about environmental issues associated with manufacturing and disposal of synthetic materials. For convenience of wearing, particularly by young children, it is presently preferred to manufacture the cloth member 12 as a sleeve which is sized to be simply worn around the elbow 2, as shown in FIG. 1 or on the forearm 4 as shown in FIG. 2. Accordingly, the retaining means may be simply a pair of elastic bands 20, the each secured to a respective end of the sleeve 12. The sleeve 12 can be worn in direct abutting engagement with the elbow 2 or forearm 4 or can be worn on a clothing 6 covering such elbow 2 or forearm 4 as best shown in FIG. 2 as covering the forearm 4. It is also contemplated that the sleeve 12 can be worn on the upper arm and also that the sleeve 12 can be sized to cover a combination of forearm, elbow and upper arm.

The exterior surface of the sleeve 12 can contain predetermined graphics 22, printed thereon which will be suitable for use with young children. Flowers, cartoon characters, animals, children pictures and the like will be suitable for use with the article 10 of the present invention. In addition to appealing to young children, the graphics 22, preferably having colors associated therewith, will be advantageous in reducing visibility of undesirable residue left on the outer surface of the sleeve 12. Alternatively or in combination with the graphics 22, the sleeve 12 may be manufactured in a predetermined color suitable for reducing visibility of undesirable residue left on the outer surface thereof.

According to another embodiment of the invention, the sleeve 12 may be manufactured from a laminate or layered material essentially including a bottom sheet 14 which is positioned in a direct abutting engagement with a portion of an the arm or clothing 6, a top sheet 16 which is joined to the bottom sheet 14 and which is capable of permeating such bodily substance discharge therethrough, and a bodily substance discharge holding core 18 positioned between the top sheet 16 and the bottom sheet 14.

One example of such layered material is taught in U.S. Pat. No. 6,579,273 issued to Dupuy for use with a reusable diaper which is manufactured by Fuzzi Bunz World of Sneads Ferry, N.C. Teachings of U.S. Pat. No. 6,579,273 is incorporated into this document by reference thereto. However, the present invention contemplates that any other absorbent laminate or layered type materials presently used in diapers, sanitary napkins, incontinence guards and the like can be employed in the present invention for absorbing bodily substance discharge. For example, U.S. Pat. No. 6,569,136 issued to Tao et al. and which is incorporated into this document by reference thereto discloses another type of a layered absorbent article. It will be appreciated that the article 10 may be constructed from a biodegradable laminate or layered material.

It will be also understood that the article 10 can be disposed after a single use or a predetermined number of uses or can be repeatedly cleaned and reused.

Figure 5:
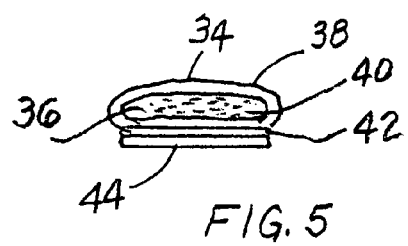
FIG. 5 is a side elevation view of the article of FIG. 3, particularly showing its structural elements.
Figure 3:
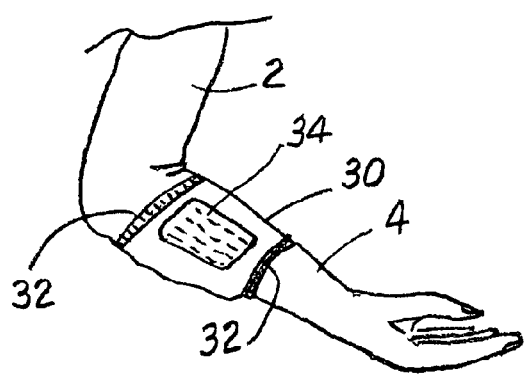
FIG. 3 is a perspective view of an article for absorbing bodily substance discharge from and delivering medicinal substance to mouth or nose which is constructed according to another embodiment of the invention and which is shown as being worn on the forearm of the user.
Figure 4:
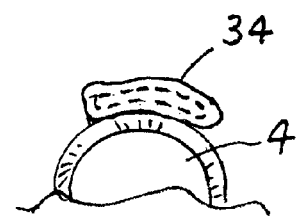
FIG. 4 is a side elevation view of the article of FIG. 3.

The reader's attention is now directed to FIGS. 3-5, wherein there is shown an article 10 for absorbing bodily substance discharge which is constructed according to yet another embodiment of the invention. Such article 10 includes a base member 30 which is positioned in an abutting engagement with a portion of the arm or clothing. Preferably, the base member 30 is manufactured as a sleeve from a breathable type material which is held in place by a pair of elastic bands 32. A pad 34 includes a backing sheet 36, a top sheet 38 which is joined to the backing sheet 36 and which is capable of passing such bodily substance discharge therethrough and a bodily substance discharge holding core 40 positioned between the top sheet 38 and the backing sheet 36. The pad 34 can be manufactured from any materials described above for manufacturing the sleeve 12. Thus, the pad 34 may be manufactured as a disposable or reusable type. The pad 34 of a disposable type is intended to be disposed after a single use or after a predetermined number of uses.

An attachment means is disposed on and secured to the backing sheet 36 disposed adjacent the surface of the base member 30 for releaseably attaching the pad 34 thereto. It is presently preferred for such attachment means to include simple adhesive 42, for example of the type presently used in feminine hygiene napkins.

An optional protective liner 44 may be employed to cover the adhesive 42. When employed, the liner 44 is removed by the user prior to attaching the backing sheet 36 to the base member 30.

Figure 6:
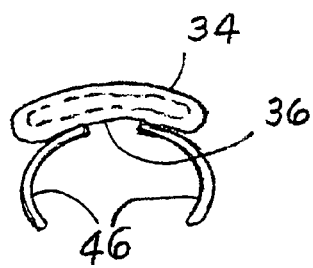
FIG. 6 is a side elevation view of an article for absorbing bodily substance discharge from and delivering medicinal substance to mouth or nose which is constructed according to yet another embodiment of the invention.
Figure 7:
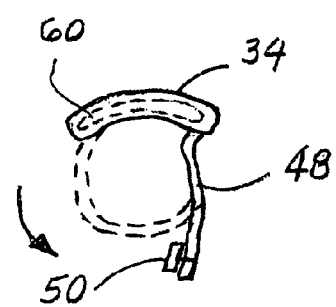
FIG. 7 is a side elevation view of an article for absorbing bodily substance discharge from and delivering medicinal substance to mouth or nose which is constructed according to a further another embodiment of the invention.

According to a further embodiment of the invention, best shown in FIGS. 6-7, the pad 34 of either disposable or reusable type can be attached directly to the forearm 4 or to the clothing 6 covering such forearm 4 either with retaining members 46 which are secured to the backing sheet 36 and which are sized to firmly but gently grip the forearm 4 during use, or with the strap 48 having a first end thereof secured to a first portion of the backing sheet 36 and having a second end thereof releaseably secured to a second portion of the backing sheet 36 for example with a hook and loop fastener 50 and which is wrapped around the forearm 4 during use.

The method of absorbing bodily substance discharge from mouth or nose includes the step of providing an article 10 capable of receiving and holding the bodily substance discharge. Then, attaching, by a user, the article to a portion of an arm or clothing. Next, positioning, by the user, the portion of the arm or the clothing having the article 10 attached thereon in front of the mouth or the nose. Finally, expelling, by the user, the bodily substance discharge into the article 10.

It is within the scope of the present invention to impregnate at least the top sheet 16 of the sleeve 12 or the top sheet 38 of the pad 34 with a medicinal substance capable of alleviating the discomfort of the user and/or soothing or calming the user coming in contact with such top sheet 16, 38. For example, medicinal essential oils, such as eucalyptus, can be used for alleviating the discomfort and clearing congestion or soothing essential oils, such as lavender, can be used for soothing or calming the user. However, other medications, aromatherapies and remedies including antiviral, antifungal, antimicrobial, antibacterial, herbal and the like may be equally employed in the present invention.

In accordance with another aspect of the invention, the article 10 having such medicinal substance incorporated therein is advantageous for soothing or calming the user even in absence of the bodily discharge. By way of an example only, the user may use the article 10 incorporating eucalyptus oil to inhale its vapors which permeate form the surface to sooth a sore throat. Or, the user may bring the surface of the article 10 into abutting engagement with the nose portion to alleviate redness which usually remains after the running nose condition ceased to exist. The article 10 which used for delivering medicinal substance to mouth or nose may be simply and economically manufactured from cotton or gauze material commonly used in health establishment.

It will be appreciated that the article 10 constructed in accordance with various embodiments of the present invention is manufactured in different sizes to be worn by children and adults alike.

It is also within the scope of the present invention to provide an annunciation device 60 which is secured between the top sheet 16, 38 and the backing sheet 14, 36 and which has a motion detector mounted therewithin and a sound generating means which is responsive to the motion detector detecting a motion for generating a predetermined audible sound reminding the user to use the article 10 for absorbing such bodily substance discharge from such mouth or nose. For the sake of brevity, the structural description of such device 60 is omitted from this document as such devices are commonly known in the toy art to produce a prerecorded sound when motion of the toy is detected. For example, one type of the device 60 is disclosed in U.S. Pat. No. 4,479,329 issued to Fraden and which is incorporated into this document by reference thereto.

Figure 8B:
FIGS. 8a-8b illustrate a toy doll suitable for teaching a young child in use of the article for absorbing bodily substance discharge from and delivering medicinal substance to mouth or nose.
Figure 8A:
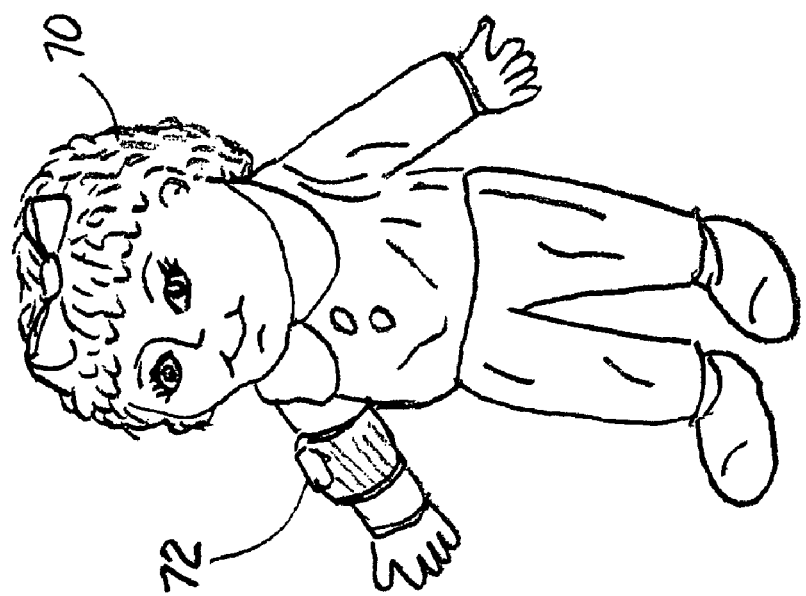

Advantageously, the toy doll 70 which is constructed according to U.S. Pat. No. 4,479,329 and which is best shown in FIGS. 8a and 8b can be employed for teaching the young children in proper techniques of using the article 10 of the present invention by incorporating either the actual article 10 or its look-alike version 72 and by producing appropriate arm motion replicating the arm motion of the child and also by generating and emitting predetermined instructional messages. Although the toy in U.S. Pat. No. 4,479,329 is illustrated as being motion activated, a switch means 74 may be provided for selectively activating and deactivating the toy 70.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

I claim:

1. A method of delivering at least one medicinal substance to mouth or nose, said method consisting the steps of:
   (a) providing a hollow sleeve manufactured from a material capable of absorbing said at least one medicinal substance;
   (b) selecting said at least one medicinal substance from a group consisting of medicinal essential oils, soothing essential oils, antiviral medication or remedies, antifungal medication or remedies, antimicrobial medication or remedies, antibacterial medication or remedies and herbal remedies;
   (c) incorporating said at least one medicinal substance into said sleeve;
   (d) attaching in elastic manner, by a user, said sleeve on a portion of an arm in direct abutting engagement therewith or over an article of clothing;
   (e) positioning, by said user, said portion of said arm having said sleeve attached thereon in front of said mouth or said nose; and
   (f) inhaling, by said user, vapors of said at least one medicinal substance permeating from exterior surface of said sleeve.

2. The method, according to claim 1, wherein said material is a cotton or hemp/cotton combination.

3. The method, according to claim 1, wherein said material is a washable material.

4. The method, according to claim 1, wherein said material includes an inner liner.

* * * * *